United States Patent [19]
Mongeon et al.

[11] Patent Number: 4,569,469
[45] Date of Patent: Feb. 11, 1986

[54] BONE STAPLER CARTRIDGE

[75] Inventors: Douglas R. Mongeon, Orange, Calif.; Edward P. Skwor, Savage, Minn.

[73] Assignee: Minnesota Mining and Manufacturing Company, Saint Paul, Minn.

[21] Appl. No.: 701,970

[22] Filed: Feb. 15, 1985

[51] Int. Cl.$^4$ ............................................. A61B 17/00
[52] U.S. Cl. .................................... 227/19; 206/338; 227/120; 227/121; 227/DIG. 1
[58] Field of Search .................. 128/334 R; 206/338, 206/339, 340; 227/DIG. 1, 19, 120, 156, 121

[56] References Cited
U.S. PATENT DOCUMENTS

| | | | |
|---|---|---|---|
| 2,874,384 | 2/1959 | Krone | 227/DIG. 1 |
| 4,202,480 | 5/1980 | Annett | 227/8 |
| 4,412,539 | 11/1983 | Jarvik | 128/325 |
| 4,500,025 | 2/1985 | Skwor | 227/19 |

Primary Examiner—Paul A. Bell
Attorney, Agent, or Firm—Donald M. Sell; James A. Smith; William L. Huebsch

[57] ABSTRACT

A bone stapler including a staple cartridge that, when removed from the stapler, insures that no staple can remain in the stapler, and is held in place by a rotatable locking member that in one position can pass through an opening in a wall of the stapler and can then be rotated to hold the cartridge in place.

6 Claims, 11 Drawing Figures

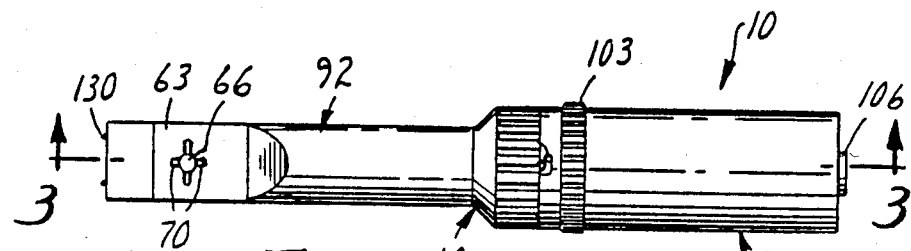
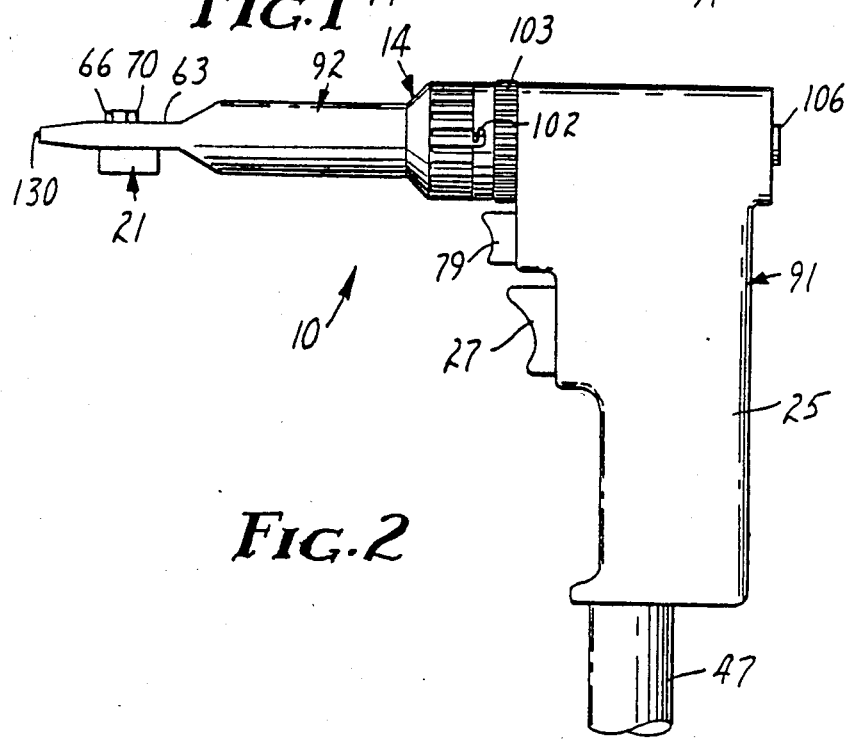
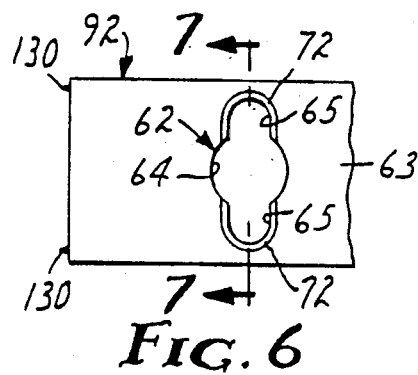 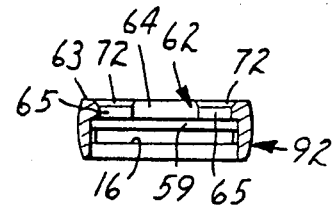

BONE STAPLER CARTRIDGE

TECHNICAL FIELD

This invention relates to staple cartridges used in devices for driving staples.

BACKGROUND INFORMATION

U.S. Patent Application Ser. No. 508,588, filed June 28, 1983, and U.S. Patent Applications Ser. Nos. 514,928 and 514,929 filed July 18, 1983 describe generally the same bone stapling device described in this application which has numerous novel design features which facilitate driving staples into bone portions during surgery. Generally, the bone stapler described in both those applications and in this application are staplers of the type adapted for use with generally U-shaped staples. The staplers comprise a housing having a passageway extending from an inlet opening to an outlet opening, which passageway is adapted to guide a single staple moved from the inlet to the outlet opening. Means are provided for biasing a stack of staples into the inlet opening, together with a driver having an end portion adapted to engage the central portion of a staple. The driver is mounted on the housing for sliding movement between a load position spaced from the inlet opening to afford movement of one of the staples of the stack into the passageway, along the passageway with the end portion of the driver pushing the staple, and to an eject position at which the driver pushes the staple out the outlet opening. Also manually activatable drive means are provided for rapidly and forcefully propelling the driver along the passageway from its load position to its eject position to move a staple from the inlet opening to the outlet opening and drive the staple into portions of bone adjacent the outlet opening.

The novel features described in the above mentioned prior applications include a removable cartridge which precludes leaving a staple in the stapler that could be inadvertently driven after the cartridge is removed. The case in that cartridge comprises guide wall means defining an inner surface at the end of a stack of staples opposite a follower and side walls projecting normal to the inner surface, which side walls have opposed transverse openings at the inner surface and aligned with the passageway when the cartridge is in the stapler. The inner surface defined by the guide wall means defines a portion of the passageway for the driver at the inlet opening, with the driver being movable through the transverse openings and along the inner surface between its load and the eject positions. Thus because all of the staples remain within the cartridge until they are driven, the user can be assured that all the staples are removed from the stapler when the cartridge is removed.

DISCLOSURE OF THE INVENTION

The present invention provides a cartridge and a stapler generally of the types described above, but which include novel attachment means for releasably attaching the cartridge to the stapler that are less expensive to manufacture and significantly easier to use than the attachment means described in the applications described above.

According to the present invention there is provided a cartridge adapted for use in a stapler for driving generally U-shaped staples, which stapler comprises a housing having a passageway extending from an inlet opening to an outlet opening adapted to guide a single staple between those openings, a driver mounted on the housing for sliding movement between a load position spaced from the inlet opening to afford movement of one of the staples into the passageway, along the passageway pushing the staple to an eject position at which the driver pushes the staple out the outlet opening; and manually activatable drive means for propelling the driver along the passageway from its load to its eject position. The housing includes a support wall having an inner surface defining a socket adapted to receive the cartridge at the inlet opening, which support wall has a through opening between its inner and outer surfaces. The cartridge includes a case comprising a guide wall defining an inner surface and side walls projecting generally normal to the inner surface, the side walls having opposed transverse openings at the inner surface. The guide wall is adapted to be received in the socket with the inner surface defining a portion of the passageway at the inlet opening and the transverse openings aligned with the passageway so that the driver can be moved through the openings and along the inner surface between its load and eject positions. The cartridge also includes a stack of staples within the case, a follower on the side of the stack of staples opposite the passageway and movable within the case with the stack of staples, a spring for biasing the follower and the stack of staples toward the inner surface, and the novel attachment means adapted for releasably retaining the case in engagement with the housing. Those attachment means comprise a locking member mounted on the guide wall for rotation about an axis generally normal to the inner surface, projecting from the side of the guide wall opposite the inner surface, having a spacing portion of a first maximum radius extending from the guide wall for a first predetermined distance about equal to the distance between the inner and outer surfaces of the support wall with the first maximum radius affording rotation of the spacing portion within a first central portion of the opening in the support wall, and having a locking portion with at least one lug projecting beyond the maximum radius at the distal end of the first portion. The lug is adapted to pass through a second portion of the opening through the support wall in a release position of the locking member relative to the case, and is adapted to engage the second surface of the support wall at positions spaced from its release position to hold the cartridge on the housing.

Preferably the locking portion of the locking member has two opposite lugs projecting beyond the maximum radius of the spacing portion, the opening through the support wall has two opposite second portions adapted to pass the lugs in the release portion of the locking member, and the housing includes cam surfaces around the second portions of the opening and intersecting the outer surface of the support wall to facilitate rotation of the locking member from its release to its locking position when a major portion of the spacing portion of the locking member is in the opening.

BRIEF DESCRIPTION OF THE DRAWING

The above and additional novel features will be described with reference to the accompanying drawing wherein like numbers refer to like parts in the several views and wherein:

FIG. 1 is a top view of a bone stapler including the improved cartridge according to the present invention;

FIG. 2 is a side view of the bone stapler of FIG. 1;

FIG. 6 is an enlarged fragmentary view of a barrel assembly on the bone stapler of FIG. 1 from which the cartridge has been removed;

FIG. 7 is a sectional view taken approximately along lines 7—7 of FIG. 6;

DETAILED DESCRIPTION

Figure 3:
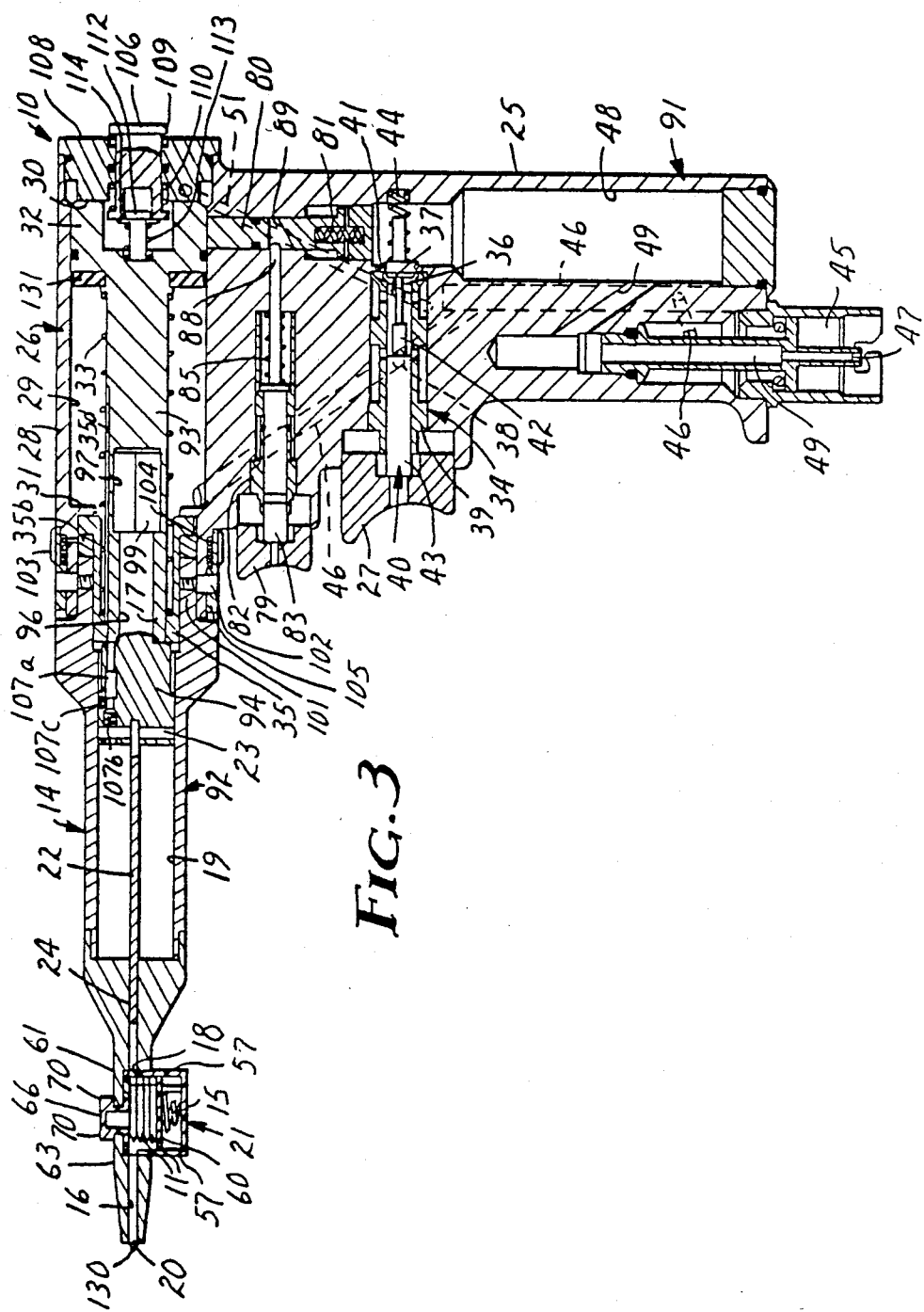
FIG. 3 is an enlarged sectional view taken along line 3—3 of FIG. 1.
Figure 4:
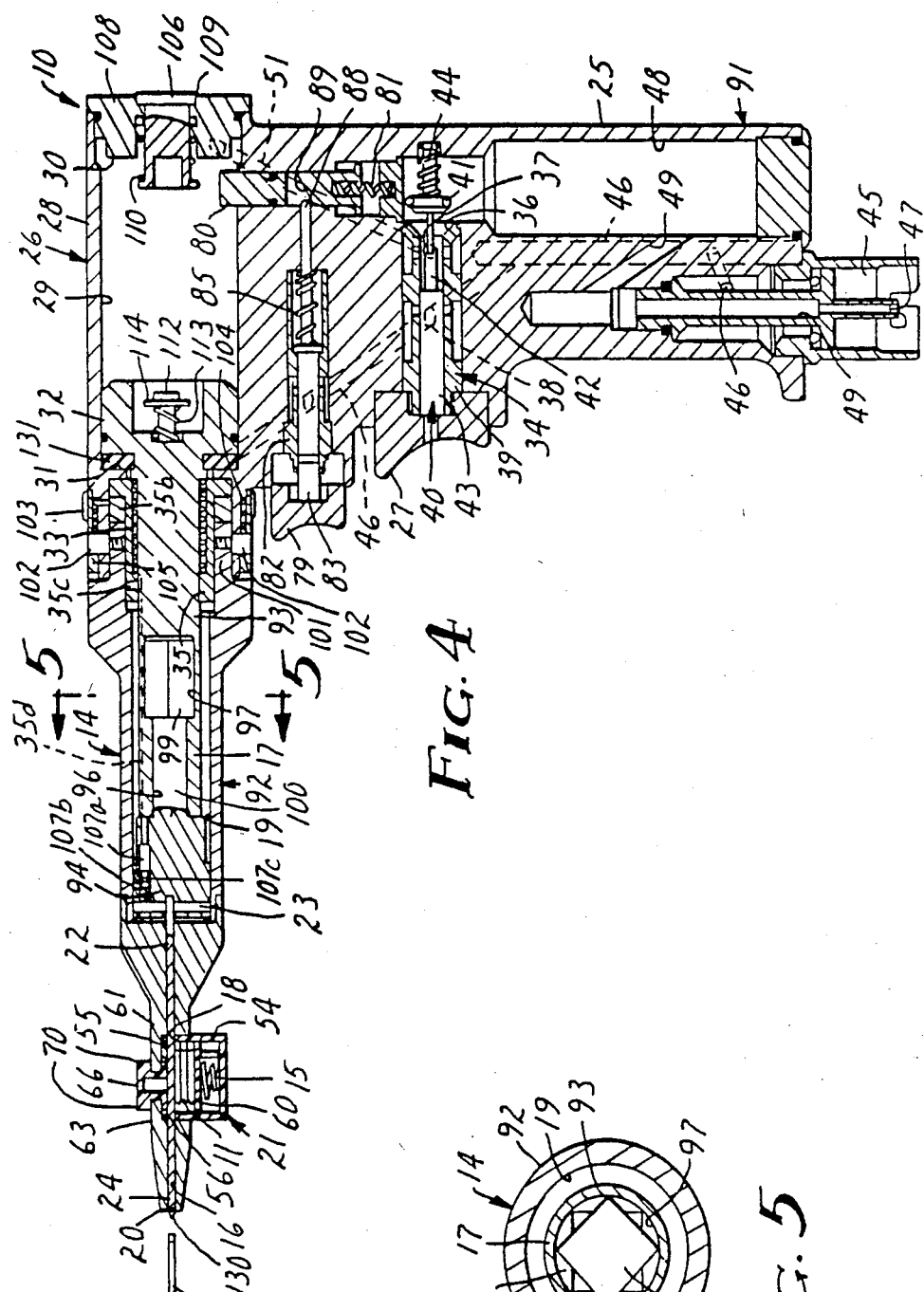
FIG. 4 is an enlarged sectional view taken along line 3—3 of FIG. 1 and similar to FIG. 3, but in which drive means has been activated to drive a staple.

Referring now to FIGS. 1 through 4 there is illustrated a bone stapler to which is attached a cartridge 21 according to the present invention, which stapler is generally designated by the reference numeral 10.

Figure 11:
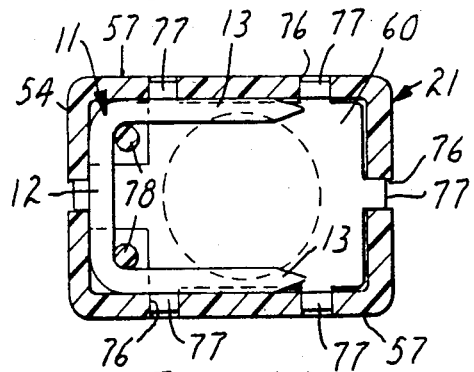
FIG. 11 is a sectional view taken approximately along line 11—11 of FIG. 9.

The stapler 10 is adapted for use with generally U-shaped staples 11 (FIG. 11). Each of the staples 11 comprises a central portion 12 and two generally parallel leg portions 13 having pointed distal ends and projecting generally in the same direction from opposite ends of its central portion 12, which leg portion 13 preferably diverge by about 1 or 2 degrees so that the driven staple will provide a compressive effect on portions of bone joined by it. Generally the stapler 10 comprises a pistol-shaped housing 14 having a passageway 16 (FIGS. 3 and 4) extending from an inlet opening 18 to an outlet opening 20, which passageway 16 is adapted to guide one of the staples 11 from the inlet opening 18 to the outlet opening 20 with the distal ends of the staple 11 leading. Means are provided for biasing a stack of the staples 11 contained in the replaceable cartridge 21 into the inlet opening 18. A driver 22 having an end portion 24 adapted to engage the central portion 12 of one of the staples 11 is mounted on the housing 14 for sliding movement between a load position (FIG. 3) with the driver 22 spaced from the inlet opening 18 to afford movement of one of the staples 11 into the passageway 16, along the passageway 16 with its end portion 24 pushing the staple, to an eject position (FIG. 4) at which the end portion 24 of the driver 22 pushes the staple 11 out of the outlet opening 20 and at which eject position the driver 22 is stopped. Drive means including an air cylinder assembly 26 powered by air under greater than atmospheric pressure and adapted to be manually activated by pulling an actuating trigger 27 into a handle portion 25 of the housing 14 are provided for rapidly and forcefully propelling the driver 22 along the passageway 16 from the load position to the eject position to move the staple 11 from the inlet opening 18 to the outlet opening 20.

The driver 22 comprises a blade-like portion on which its end portion 24 is formed, and a cylindrical portion 17 that moves within a cylindrical guide bore 19 in the housing 14, to which cylindrical portion 17 the blade-like portion is attached by a pin 23 through an enlarged cylindrical part 17a of the cylindrical portion 17 that slides in close fitting engagement in the guide bore 19 and has through ports (now shown) to allow air to escape from in front of it.

The drive means for propelling the driver 22 comprises the air cylinder assembly 26 which includes a cylinder 28 partially defined by a cylindrical inner surface 29 of the housing 14 concentric with the guide bore 19, which inner surface 29 has first and second ends 30 and 31, and a piston 32 within the cylinder 28 integral with an end portion of the driver 22 opposite its end portion 24. This piston 32 is in slidable sealing engagement with the cylindrical inner surface 29, and is movable along the inner surface 29 between a first position adjacent the first end 30 of the cylinder 28 at which the piston 32 is located when the driver 22 is in its load position and to which the piston 32 is biased by a main spring 33 within the cylinder 28 and the housing 14; and a second position adjacent the second end 31 of the cylinder 28 at which the piston 32 is positioned when the driver 22 is in its eject position.

The end of the main spring 33 opposite the piston 32 is supported against an annular inwardly projecting ledge on a guide collar 35 which guide collar 35 has an outwardly projecting rim fixed against an inwardly projecting lip in the housing 14 by an anchor ring 35b threadably engaged with the housing 14. The inner surface of the inwardly projecting ledge is in close engagement around the driver 22 and carries a pin 35c positioned in a longitudinal groove 35d in the driver 22 to allow longitudinal movement of the driver 22 between its load and eject positions while the pin 35c prevents rotation of the driver 22 relative to the housing 14.

The actuating trigger 27 by which the air cylinder assembly 26 is actuated is included in a valve assembly 34 comprising the housing 14 having a bore opening through the front of its handle portion 25 in which a guide spool 39 is fixed and having an inlet port 36 and first and second outlet ports 37 and 38 communicating with the bore. An actuator 40 coupled to the actuating trigger 27 by a set screw (not shown) is manually movable within the guide spool 39 from an outer blocking position (FIG. 3) at which an O-ring 41 around a groove in the actuator 40 engages a seat around and closes the inlet port 36, and clearance between a small diameter portion 42 of the actuator 40 and the inner surface of the guide spool 39 connects the outlet ports 37 and 38 through transverse passageways in the guide spool 39; and an inner activate position (FIG. 4) with the O-ring 41 separated from the seat to connect the inlet port 36 and the first outlet port 37 past the small diameter portion 42 of the actuator 40, and at which a larger diameter 43 portion of the actuator 40 essentially closes the transverse passageways in the guide spool 39 leading to the second outlet port 38. A spring 44 provides means for biasing the actuator 40 to its outer blocking position, against which spring 44 the actuator 40 may be manually moved or pulled to its activate position by the actuating trigger 27. The housing 14 has an outlet passageway 46 which communicates with the cylinder 28 adjacent its second end 31, communicates with the second outlet port 38, and is adapted to be coupled to a portion of a hose (not shown) leading to air at atmospheric pressure through a conventional surgical air inlet connector, a female half 45 of which is formed in the housing 14. The housing 14 also has an inlet passageway 47 including an enlarged reservoir portion 48

(which provides sufficient air volume to quickly move the piston 32) coupled to the inlet port 36 and a smaller portion 49 adapted to be coupled to a source of air under greater than atmospheric pressure through the female coupling half 45. Also included is a transfer passageway 51 coupled between the first outlet port 37 and communicating with the cylinder 28 adjacent its first end 30. Thus, when the stapler 10 is activated by the actuating trigger 27 being pulled into the housing 14 to move the actuator 40 to its activate position (FIG. 4), air under greater than atmospheric pressure in the reservoir 48 and from the supply will flow through the inlet port 36, past the small diameter actuator portion 42 and out the transfer passageway 51 to the first end 30 of the cylinder 28, while the larger diameter portion 43 of the actuator 40 precludes any significant amount of the high pressure air from escaping into the outlet passageway 46. As the piston 32 starts to move from its first to its second position under the influence of the high pressure air, air between the piston 32 and the second end 31 of the cylinder 28 will flow out the outlet passageway 46 and to the atmosphere through a hose (not shown) coupled at the female coupling half 45. When the actuating trigger 27 is subsequently released (FIG. 3), the actuator 40 will return to its deactivated position under the influence of the spring 44 so that the inlet port 36 is closed, and the first and second outlet ports 37 and 38 are connected past the small diameter portion 42 of the actuator 40 so that the high pressure air can escape from behind the piston 32 via the transfer passageway 51, bore 35 and outlet passageway 46, and air at atmospheric pressure as needed can flow to the front of the piston 32 via the outlet passageway 46.

The cartridge 21, best seen in FIGS. 8 through 11, includes a case 54 comprising a guide wall 55 defining an inner surface 56 at one end of the stack of staples 11, side walls 57 projecting normal to the inner surface 56, and an end wall 53 opposite the guide wall 55. The side walls 57 have opposed transverse openings 58 adjacent the inner surface 56 and an end portion of the cartridge 21 including the guide wall 55 is received in a socket 59 defined by an inner surface of a support wall 61 included in the housing 14 with the transverse openings 58 aligned with the passageway 16 and the inner surface 56 defining a portion of the passageway 16 at its inlet opening 18 so that the driver 22 is movable through the transverse openings 58 and along the inner surface 56 between its load and eject positions. The cartridge 21 further includes a follower 60 on the side of the stack of staples 11 opposite the inner surface 56 and passageway 16, which follower 60 is movable within the case 54 with the stack of staples 11, and the coil spring 15 between the end wall 53 of the case 54 and the follower 60 for biasing the follower 60 and the stack of staples 11 toward the inner surface 56. Thus as the driver 22 moves through he transverse openings 58 and along the inner surface 56 during movement from its load to its eject position, the driver 22 will carry with it the staple 11 pressed against the inner surface 56 by the follower 60 and spring 15. When removed, the cartridge 21 will carry with it all of the staples 11 remaining in the stapler 10 so that, with the cartridge 21 removed, it will be impossible to inadvertently fire a staple 11 from the stapler 10.

Means for releasably retaining the cartridge 21 in the socket 59 in the housing 14 is provided by the support wall 61 (best seen in FIGS. 6 and 7) having a through opening 62 between its inner surface defining the socket 59 and an outer surface 63 generally parallel to its inner surface at the bottom of the socket 59, which through opening 62 has a circular central first opening portion 64 and two generally U-shaped opposed second opening portions 65 on opposite sides of the central opening portion 64; and the cartridge 21 (best seen in FIGS. 8-11) having a locking member 66 mounted on the guide wall 55 for rotation about an axis generally normal to the inner surface 56, projecting from the side of the guide wall 55 opposite the inner surface 56, having a spacing portion 68 of a first maximum radius extending from the guide wall 55 for a first predetermined distance about equal to the distance between the inner and outer surfaces of the support wall 61 with the first maximum radius affording rotation of the spacing portion 68 within the central first opening portion 64, and having a locking portion with at least one, and as illustrated, two lugs 70 projecting beyond the maximum radius at the distal end of the spacing portion 68. The lugs 70 are adapted to pass through the second portions 65 of the opening 62 in a release position of the locking member 66 relative to the case 54, and have a surface adjacent the support wall 61 in engagement with the outer surface 63 of the support wall 61 at positions of the locking member 66 spaced from its release position to hold the cartridge 21 in the socket 59 on the housing 14.

As is best seen in FIGS. 6 and 7, preferably the housing 14 includes a cam surface 72 around each of the second portions 65 of the opening 62. The cam surfaces 72 intersect the outer surface 63 of the support wall 61 and facilitate rotation of the locking member 66 from its release portion to a position with the lugs 70 along the outer surface 63 of the support wall 61 when the spacing portion 68 of the locking member 66 is in the opening 62. Upon such rotation, engagement between the lugs 70 and the cam surfaces 72 will pull the cartridge 21 firmly into the socket 59, eliminating the necessity for the user to press the cartridge 21 fully to that position prior to rotating the locking member 66.

As is best illustrated in FIGS. 8-11, the cartridge 21 includes a stack of staples 11, the coil spring 15 and four polymeric moldings that provide the follower 60, the guide wall 55 and a cup-shaped member that includes the side walls 57 and the end wall 53 and is fused to the guide wall 55 to form the case 54, and the locking member 66. The locking member 66 has an annular rim 73 on its end opposite the lugs 70, which rim 73 is rotatably received in a recess from the inner surface 56 of the guide wall 55. The guide wall 55 has an orifice shaped to pass the lugs 70 and spacing portion 68 of the locking member 66 by slightly deflecting a central portion of the guide wall 55 defining a central portion of the orifice, which central portion of the guide wall 55 will move into a shallow groove 74 around the locking member 66 adjacent the annular rim 73 where the guide wall 55 is retained while the locking member 66 is freely rotatable relative to the guide wall 55.

The side of the follower 60 opposite the staples 11 has a circular recess that receives a large end of the spring 15, whereas the smaller end of the spring 15 is located around a post 75 projecting from the end wall 53. The spring 15 is tapered between the follower 60 and the end wall 53 to reduce the range of pressures that it will apply to the staples 11 as the height of the stack of staples 11 decreases, and to minimize its compressed height and thereby the height of the cartridge 21.

Means for guiding the follower 60 are provided by grooves 76 in the side walls 57 disposed at right angles to the guide wall 55, shoes 77 formed on the edges of the follower 60 adapted to slide within the grooves 76, and two parallel pins 78 projecting from the end wall 53 received in openings in the follower 60. The shoes 77 on the sides of the follower 60 have upwardly projecting parts that prevent the follower 60 from being pushed into the path of the driver 22 after the last staple 11 is ejected from the cartridge 21.

The bone stapler 10 includes blocking means for automatically preventing movement of the driver 22 to its load position from an intermediate position between its load and eject positions with a portion of the driver 22 projecting partially through the cartridge 21 and across the inlet opening 18 to the passageway 16 after the driver 22 has moved from its load to its eject position. Thus, with the driver 22 initially in its load position, the drive means may be manually activated a first time by pulling the actuating trigger 27 to drive a staple 11 through the outlet opening 20 and may subsequently be manually activated an additional number of times by pulling the actuating trigger 27 so that the driver 22 will be again propelled to is eject position to further impact that driven staple 11 as may be needed to fully seat the driven staple 11, without driving an additional staple 11 from the cartridge 21. Also included are reset means manually activated by a reset member or trigger 79 for resetting the blocking means to allow return movement of the driver 22 from its intermediate to its load position so that another staple 11 may be driven.

The blocking means in the bone stapler 10 comprises a plunger 80 axially slidably mounted in a bore in the housing 14 communicating with the cylinder 28 at its first end 30 for movement in a direction normal to the axis of the cylinder 28 between a nonblocking position (FIG. 3) spaced from within the cylinder 28, to a blocking position (FIG. 4) partially within the cylinder 28 to which the plunger 80 is biased by a spring 81, so that engagement between the plunger 80 and the side of the piston 32 adjacent the first end 30 of the cylinder 28 will define the intermediate position for the piston 32. When the piston 32 is in its first position corresponding to the load position of the driver 22, the periphery of the piston 32 will retain the plunger 80 in its nonblocking position in opposition to the biasing of the spring 81 (FIG. 3). Upon movement of the piston 32 from its first position toward its second position corresponding to the eject position of the driver 22, however, the plunger 80 will automatically move to its blocking position under the influence of the spring 81 (FIG. 4) to thus preclude the piston 32 from returning to its first position and thus preclude the driver 22 from returning to its load position until the reset means is operated by the reset trigger 79.

The reset means comprises the reset trigger 79 fastened by a set screw (not shown) to an outer end portion of a spindle 83, which spindle 83 is slidably mounted in a sleeve 82 fixed in a bore opening through the front of the handle portion 25 of the housing 14 for longitudinal sliding movement between an outer position (FIGS. 3 and 4) and an inner position (not shown). Also included in the reset means are means in the form of a spring 85 for biasing the reset trigger 79 to its outer position, and cam means on the spindle 83 and reset trigger 79 for moving the plunger 80 from its blocking to its nonblocking position against the bias of spring 81 upon manual movement of the spindle 83 from its outer to its inner position via the reset trigger 79. The cam means comprise a semispherical tip 88 on the inner end of the spindle 83, and a surface 89 inclined with respect to the axis of the spindle 83 partially defining a slot in the plunger 80 in which the tip 88 is received to prevent rotation of the plunger 80. The slot in the plunger 80 is sufficiently long to afford movement of the plunger 80 from its nonblocking to its blocking position under the influence of the spring 81 after the driver moves toward its eject position. With the plunger 80 in its blocking position the reset trigger 79 may be manually pulled toward the handle portion 25 of the housing 14 which will cause the tip 88 to engage the inclined surface 89 so that the plunger 80 will be pulled back to its nonblocking position. This will allow the piston 32 to return to its first position, and cause the driver 22 to return to its load position under the influence of the main spring 33.

The bone stapler 10 is designed to afford driving staples of different sizes in that it is made in two separable assemblies including a handle assembly 91 which includes the drive means mounted on one part of the housing 14, and a barrel assembly 92 which defines the passageway 16 and receives the cartridge 21 for staples 11 of one size on another part of the housing 14. Means are provided for releasably engaging the parts of the housing 14, and the driver 22 is separable into a second part 93 included in the handle assembly 91 and connected to the piston 32, and a first part 94 including its end portion 24 which is included in the barrel assembly 92. Different barrel assemblies that each have a housing part defining a passageway, a driver part and accept cartridges of a different size of staple may be substituted for the barrel assembly 92 to afford driving staples of different sizes.

Figure 5:
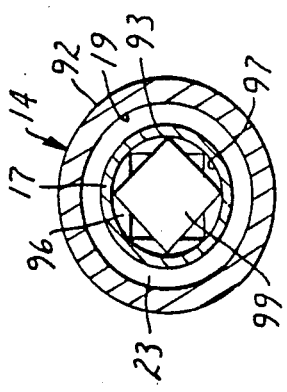
FIG. 5 is an enlarged sectional view taken approximately along lines 5—5 of FIG. 4.
Figure 8:
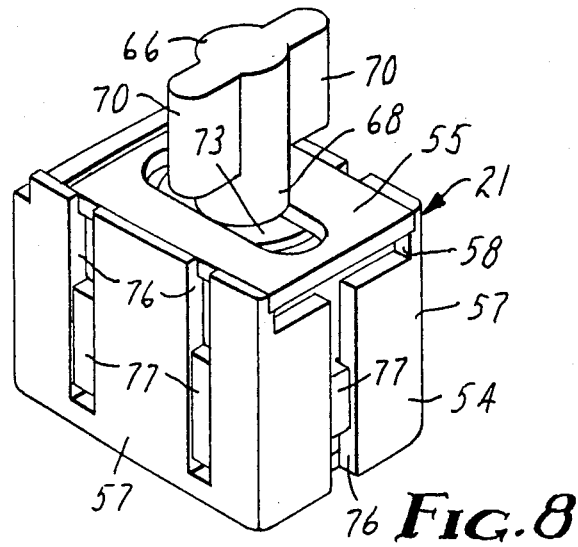
FIG. 8 is an enlarged perspective view of the cartridge according to the present invention shown in combination with the stapler in FIGS. 1 through 4.
Figure 9:
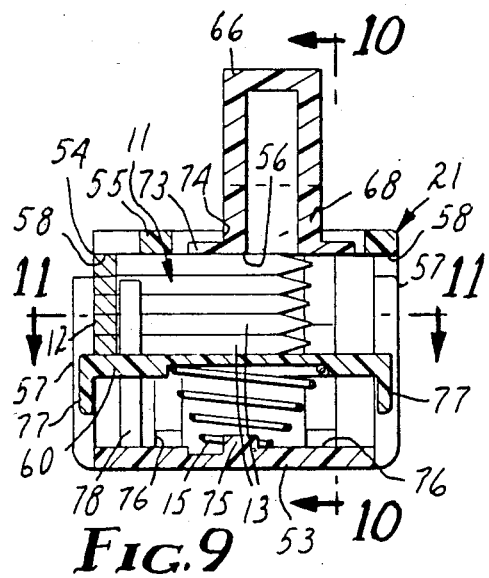
FIG. 9 is a vertical sectional view of the cartridge shown in FIG. 8.
Figure 10:
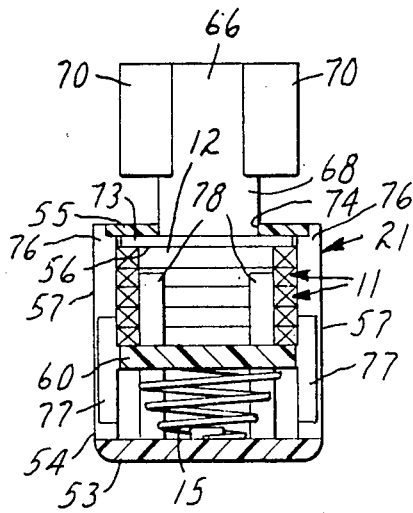
FIG. 10 is a sectional view taken approximately along line 10—10 of FIG. 9.

Means are provided for releasably engaging the first and second parts 94 and 93 of the driver 22 and for releasably engaging the handle and barrel assemblies 91 and 92. These means comprise walls on the first part 94 of the driver 22 opposite its end portion 24 defining a socket with an outer portion 96 having a square cross section and an inner portion 97 with a circular cross section; and a tip on the first part 94 of the driver 22 including a distal square portion 99 adapted to slide within the socket through its outer portion 96 and to rotate in its inner portion 97 out of alignment with the outer portion 96 (see FIG. 5) with the walls defining the outer portion 96 around a reduced diameter cylindrical portion 100 of the driver's first part 94. The part of the housing 14 included in the barrel assembly 92 includes a collar 101 at its end opposite the outlet opening 20 received in a socket in the part of the housing 14 included in the handle assembly 91 with the square portion 99 of the tip out of alignment with the outer portion 96 of the wall defining the socket, with four evenly spaced radially outwardly projecting pins 102 fixed on the collar 101 received in four longitudinally extending slots opening through the end of the housing part included in the handle assembly 91, and with hooks 105 on a ring 103 mounted for rotation about its axis on the housing part included in the handle assembly 91 in engagement with the pins 102 to releasably latch the handle and barrel assemblies 91 and 92 together. The barrel assembly 92 can thus be located at different orientations displaced 90 degrees from each other with respect to the handle assembly 91 to provide various orientations of a driven staple 11 relative to the handle portion 25 of the housing 14. To release the handle and barrel assemblies 91 and 92 from each other, the ring 103 is rotated against the bias of a coil spring 104 to move the hooks 105 from around the pins 102. The handle and barrel assemblies 91 and 92 are pulled apart axially of the driver 22 which pulls the pins 102 from the slots in which they are received and pulls the part of the housing 14 on the barrel assembly 92 along the driver 22 until an inwardly projecting lip (not shown) on that part of the housing 14 engages the end of the enlarged part 17 of the driver 22 adjacent the piston 32, at which position a pin 107a carried by the driver portion 17 is moved by a spring 107b so that a ball 107c will be moved into housing a groove in the housing 14, which engagement will keep the end plug 23 from moving into the guide bore 19 after the handle and barrel assemblies 91 and 92 are separated. The handle and barrel assemblies 91 and 92 are then rotated about 45 degrees relative to each other about the axis of the driver 22 to align the square position 99 of the tip with the outer portion 96 of the socket, whereupon the tip may be pulled from the socket and the assemblies 91 and 92 may be separated. Reengagement of the handle and barrel assemblies 91 and 92 is accomplished by reversing the steps listed above which will cause a cam surface on the end of the first part 92 of the driver 22 around the end of the socket to move the pin 107a against the spring 107b to release the driver 22. Upon pressing the pins 102 into the slots, camming surfaces 105b on the hooks 105 will cause the collar 101 to automatically rotate to engage the hooks 105 around the pins 102.

The bone stapler 10 also includes means for indicating to a user ready to fire the stapler 10 whether the driver 22 is in its load position from which a staple 11 can be driven or in its intermediate position. An indicating spool 106 is centrally slidably mounted in a removable plug 108 providing a portion of the housing 14 at the first end 30 of the cylinder 28. The indicating spool 106 is slidably between an inner position with a flange 109 at its outer end against the outer surface of the plug 108 to which the indicating spool 106 is biased by a spring 110, and an outer position with a portion of the spool 106 adjacent the flange 109, which is painted red, projecting from the plug 108. The piston 32 carries a central headed pin 112 at its end adjacent the first end 30 of the cylinder 28 around which pin 112 is a slidable washer 114 biased against the head of the pin 112 by a spring 113 with a greater spring constant than the spring 110. When the driver 22 is in its load position, the head of the pin 112 will enter an opening in the spool 106 while the washer 114 will be pressed against the adjacent end of the indicating spool 106 under the influence of the spring 113 causing the spool 106 to move to its outer position at which its red periphery indicates that the driver 22 is in its load position. When the driver 22 moves away from its load position, the indicating spool 106 will move to its inner position under the influence of the spring 110, thereby indicating to a user that the driver 22 is in its intermediate position.

OPERATION

The operation of the bone stapler 10 by a user will now be described assuming that a cartridge 21 containing a stack of staples 11 is held in the housing 14 by the locking member 66 and the stapler 10 is connected at the coupling half 45 to a hose assembly (not shown) including a central supply of air under greater than atmospheric pressure coupled to the inlet passageway 47 and an outer hose leading to air at atmospheric pressuire coupled to the outlet passageway 46. The user can utilize a pair of pointed locating members 130 fixed to the housing 14 in positions flanking the outlet opening 20 and projecting generally parallel to the axis of the driver 22 to help position and stabilize bone portions to be stapled in the same plane. When the bone portions are thus positioned, the stapler 10 can be activated by manually pulling the actuating trigger 27 so that air under greater than atmospheric pressure is coupled through the reservoir 48, valve assembly 34 and transfer passageway 51 to the first end 30 of the cylinder 28 which will cause rapid movement of the piston 32 and thereby the driver 22 from its load position (FIG. 3) spaced from the staple inlet opening 18, and through the cartridge 21 along its inner surface 56 to push the adjacent staple 11 in the stack along the passageway 16 to the outlet opening 20 and drive that staple 11 into adjacent portions of bone (FIG. 4), the driver 22 being stopped at its eject position at the outlet opening 20 by engagement of the piston 32 with a rubber collar 131 at the second end 31 of the cylinder 28. As the piston 32 thus is moved away from the first end 30 of the cylinder 28, the plunger 80 will move into the cylinder 28 under the influence of the spring 81 so that, after the actuating trigger 27 is released and the high pressure air at the first end 30 of the cylinder 28 escapes through the transfer passageway 51, valve assembly 34 and outlet passageway 46 to the hose coupled to atmospheric pressure and the piston 32 moves back toward its first position under the influence of the main spring 33, the piston will be stopped against the periphery of the plunger 80 with the end portion 24 of the driver 22 at an intermediate position extending through the cartridge 21 so that the next staple 11 in the stack of staples 11 can not move into the inlet opening 18 to the passageway 16. The user, if desired, can then again rapidly move the driver 22 to its eject position by again pulling the actuating trigger 27 as may be desired to further drive or seat the staple 11 previously driven into the bone portions.

When the user desires to drive a second staple 11, he can pull the reset trigger 79 which will move the tip 88 of the spindle 83 against the inclined surface 89 to cam the plunger 80 out of the cylinder 28 to its nonblocking position so that the main spring 33 can return the piston 32 to its first position and thereby the driver 22 to its load position allowing the uppermost staple 11 in the cartridge 21 to move against the inner surface 56 of the cartridge 21 at the inlet opening 18 so that subsequent activating of the drive means by the actuating trigger 27 will drive that staple 11.

If the user wishes to remove the cartridge 21 because it is empty, or to insure that the stapler 10 can not fire another staple 11, or to insert staples with different length leg portions 13, he may do so by manually rotating the locking member 66 to its release position with its lugs 70 aligned with the outer portions 65 of the opening 62 by pushing on one or both of the lugs 70, and then pulling the cartridge 21 from the socket 59 in the housing 14. He can then be sure that no staples 11 remain in the stapler 10, since the entire remaining stack of staples 11 (if any) remains in the cartridge 21. The same or a new cartridge 21 of staples 11 may again be loaded into the stapler 10 by inserting the cartridge 21 into the socket 59 in the housing 14 and then rotating the locking member 66 from its release position, which will cause the lugs 70 to move along the cam surfaces 72 and onto the outer surface 63 of the support wall 61 to pull the cartridge 21 fully into the socket 59 and hold it in place.

If the user wishes to drive staples of a different width along its central portion 12, he may also do that by substituting an appropriate different barrel assembly for the barrel assembly 92 being used, which different barrel assembly is adapted to accommodate staples 11 of that width. Such substitution is easily accomplished by rotating the locking collar 103 to release the two parts of the housing 14, pulling and relatively rotating the housing parts with respect to the longitudinal axis of the driver 22 (as is described in greater detail above) which will cause the square portion 99 on the first part 94 of the driver 22 to align with the square cross section portion 96 of walls defining the socket in the second part 93 of the driver 22 in which the square portion 99 is received, and pulling the first and second parts of the housing 14 and driver 22 away from each other to pull the square portion 99 from the socket and separate them. The different barrel assembly can then be assembled on the handle assembly 91 by reversing the separating steps.

The present invention has now been described with reference to one embodiment thereof. It will be appreciated that many modifications and changes can be made in the structure of the cartridge 21 and the means by which it is attached to the bone stapler 10 without departing from the spirit of the present invention; for example, the locking member could have more or less locking lugs than were described. Thus the scope of the claims in this application should not be limited by the structure of the stapler described herein, but only by the structures described by the language of the claims and their equivalents.

We claim:

1. A bone stapler adapted for use with generally U-shaped staples each comprising a central portion and two generally parallel leg portions projecting generally in the same direction from opposite ends of its central portion and having distal ends, said stapler compring:

a housing having a passageway extending from an inlet opening to an outlet opening, said passageway being adapted to guide a single staple moved from the inlet to the outlet opening with the distal ends of its legs leading;

a driver having an end portion adapted to engage the central portion of said staple and being mounted on said housing for sliding movement between a load position with the driver spaced from the inlet opening to afford movement of one of the staples into the passageway, along said passageway with said end portion pushing the staple, to an eject position at which the end portion of the driver pushes the staple out said outlet opening;

drive means adapted to be manually activated for propelling said driver along said passageway from said load to said eject position to move said staple from said inlet to said outlet opening;

said housing including a support wall having an inner surface defining a socket adapted to receive said cartridge at said inlet opening, said support wall also having an outer surface, a through opening between said inner and outer surfaces having a first opening portion and a second portion on one side of said first opening portion;

a cartridge including a case comprising a guide wall defining an inner surface and side walls projecting generally normal to said inner surface, said side walls having opposed transverse openings at said inner surface and aligned with said passageway, said guide wall being received in said socket with said inner surface defining a portion of said passageway at said inlet opening so that said driver can be moved through said openings and along said inner surface between said load and eject positions; a stack of staples within said case; a follower on the side of said stack of staples opposite said passageway and movable within said case with said stack of staples; a spring for biasing said follower and said stack of staples toward said inner surface; and means adapted for releasably retaining said case in engagement with said housing comprising a locking member mounted on said guide wall for rotation about an axis generally normal to said inner surface, projecting from the side of said guide wall opposite said inner surface, having a spacing portion of a first maximum radius extending from said guide wall for a first predetermined distance about equal to the distance between the inner and outer surfaces of said support wall with said first maximum radius affording rotation of said spacing portion within the first portion of said opening, and having a locking portion with at least one lug projecting beyond said maximum radius at the distal end of said first portion, adapted to pass through the second portion of said opening in a release position of said locking member and having a surface adjacent said support wall in engagement with the second surface of said support wall at a position spaced from said release position to hold said cartridge on said housing.

2. A bone stapler according to claim 1 wherein said locking portion has two opposite lugs projecting beyond the maximum radius of said spacing portion, said support wall has two opposite second portions of said opening adapted to pass said lugs in a release position of said locking member.

3. A bone stapler according to claim 1 wherein said housing includes a cam surface around the second portion of said opening and intersecting the outer surface of said support wall to facilitate rotation of said locking member away from said release position with a portion of said locking member in said opening.

4. A bone stapler according to claim 2 wherein said housing includes cam surfaces around the second portions of said opening and intersecting the outer surface of said support wall to facilitate rotation of said locking member away from said release position with a portion of said locking member in said opening.

5. A cartridge adapted for use in a stapler for driving generally U-shaped staples each comprising a central portion and two generally parallel leg portions projecting generally in the same direction from opposite ends of its central portion and having distal ends, which stapler comprises a housing having a passageway extending from an inlet opening to an outlet opening, said passageway being adapted to guide a single staple moved from the inlet to the outlet opening with the distal ends of its legs leading; a driver having an end portion adapted to engage the central portion of said staple and being mounted on said housing for sliding movement between a load position with the driver spaced from the inlet opening to afford movement of one of the staples into the passageway, along said passageway with said end portion pushing the staple, to an eject position at which the end portion of the driver pushes the staple out said outlet opening; and drive means adapted to be manually activated for propelling said driver along said passageway from said load to said eject position to move said staple from said inlet to said outlet opening, said housing including a support wall having an inner surface defining a socket adapted to receive said cartridge at said inlet opening, said support wall also having an outer surface, a through opening between said inner and outer surfaces having a first opening portion and a second portion on one side of said first opening portion, said cartridge including:
- a case comprising a guide wall defining an inner surface and side walls projecting generallly normal to said inner surface, said side walls having opposed transverse openings at said inner surface, said guide wall being adapted to be received in said socket with said inner surface defining a portion of said passageway at said inlet opening and said transverse openings aligned with said passageway so that said driver can be moved through said openings and along said inner surface between said load and eject positions;
- a stack of staples within said case;
- a follower on the side of said stack of staples opposite said passageway and movable within said case with said stack of staples;
- a spring for biasing said follower and said stack of staples toward said inner surface;

and means adapted for releasably retaining said case in engagement with said housing comprising a locking member mounted on said guide wall for rotation about an axis generally normal to said inner surface, projecting from the side of said guide wall opposite said inner surface, having a spacing portion of a first maximum radius extending from said guide wall for a first predetermined distance about equal to the distance between the inner and outer surfaces of said support wall with said first maximum radius affording rotation of said spacing portion within the first portion of said opening, and having a locking portion with at least one lug projecting beyond said maximum radius at the distal end of said first portion, adapted to pass through the second portion of said opening in a release position of said locking member relative to said case and having a surface adjacent said support wall adapted to engage the second surface of said support wall at a position spaced from said release position of said locking member to hold said cartridge on said housing.

6. A cartridge according to claim 5 wherein said locking portion has two opposite lugs projecting beyond the maximum radius of said spacing portion.

* * * * *